United States Patent [19]

Sobotta et al.

[11] Patent Number: 5,614,637
[45] Date of Patent: Mar. 25, 1997

[54] PROCESS FOR PREPARING 1,3-DIALKYL-5-HYDROXYOXINDOLES AND THE ETHER DERIVATIVES THEREOF

[75] Inventors: Rainer Sobotta; Rainer Schwarz; Manfred Psiorz, all of Ingelheim am Rhein, Germany

[73] Assignee: Boehringer Ingelheim KG, Ingelheim am Rhein, Germany

[21] Appl. No.: 448,222

[22] Filed: May 23, 1995

Related U.S. Application Data

[63] Continuation of Ser. No. 105,196, Aug. 9, 1993, abandoned.

[30] Foreign Application Priority Data

Aug. 8, 1992 [DE] Germany ............... 42 26 263.1

[51] Int. Cl.$^6$ .............................. C07D 209/34
[52] U.S. Cl. ................................ 548/486
[58] Field of Search .......................... 548/486

[56] References Cited

U.S. PATENT DOCUMENTS 4,791,107 12/1988 Hamer et al. ............ 514/228.2

OTHER PUBLICATIONS

March, J. Advanced Organic Chemistry, New York, John Wiley and Sons, 1985, pp. 479–480.
Julian, P.L. et al., J. American Chemical Society, 57, 1935, pp. 563–566.

*Primary Examiner*—Jacqueline Haley
*Attorney, Agent, or Firm*—R. P. Raymond; M-E. M. Devlin; A. R. Stempel

[57] ABSTRACT

The invention is directed to a process for preparing a 1,3-dialkyl-5-hydroxyoxindole of formula 1:

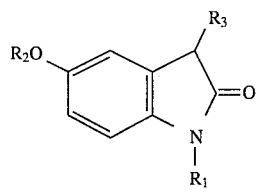

comprising heating an N-alkyl-p-alkoxy-(α-haloacyl)anilide of formula 2:

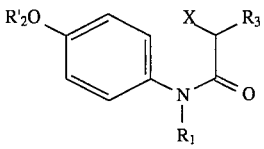

wherein the substituents are as defined herein, in the presence of an anhydrous zinc halide to a temperature in the range from about 120° C. to about 160° C., and isolating the 1,3-dialkyl-5-hydroxyoxindole prepared.

15 Claims, No Drawings

PROCESS FOR PREPARING 1,3-DIALKYL-5-HYDROXYOXINDOLES AND THE ETHER DERIVATIVES THEREOF

This is a continuation of application Ser. No. 08/105,196, filed Aug. 9, 1993, now abandoned.

The present invention relates to a method of preparing 1,3-dialkyl-5-hydroxyoxindoles and the ether derivatives thereof of formula 1 which can be carried out on an industrial scale, by cyclising N-methyl-p-alkoxy- (2-haloacyl) anilides of formula 2 according to the following formula drawing

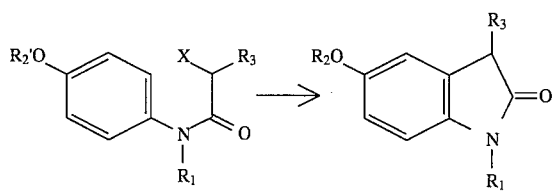

wherein formula 2 and formula 1

$R_1$ denotes $C_{1-6}$-alkyl;
$R_2$ denotes H, $C_{1-6}$-alkyl;
$R_2'$ denotes $C_{1-6}$-alkyl;
$R_3$ denotes $C_{1-6}$-alkyl and
X denotes chlorine or bromine.

$C_{1-6}$-alkyl generally denotes a branched or unbranched $C_{1-6}$-hydrocarbon radical which may be substituted with one or more halogen atoms, preferably fluorine, which may be identical to or different from one another. Examples of hydrocarbon radicals are as follows: methyl, ethyl, propyl, 1-methylethyl (isopropyl), butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Unless otherwise stated, $C_{1-4}$-lower alkyl radicals are preferred, such as methyl, ethyl, propyl, isopropyl, butyl and tert.-butyl.

The preparation of 1,3-dimethyl-5-hydroxy-oxindole or 1,3-dimethyl-5-alkoxyoxindoles is known from the prior art. Thus, Pickl et al. [P. L. Julian and J. Pikl, J. Am. Chem. Soc. 57 (1935) 563] describe a process for preparing 1,3-dimethyl-5-hydroxy-oxindole which makes it possible to produce this compound on a laboratory scale by cyclising N-methyl-p-ethoxy-α-bromopropionylanilide using anhydrous aluminium chloride.

However, this method is not suitable for industrial use as it has the following disadvantages:

the catalyst aluminium(III)chloride has to be used at least in a 6.7-fold excess per mol of educt, the hydrolysis of aluminium(III)chloride is a strongly exothermic reaction, since aluminium(III)chloride is inclined to sublimation, it is sublimated into the structure of the apparatus when the reaction mixture is heated, after which it is no longer available for cyclising, the use of aluminium(III)chloride as a catalyst involves the risk of secondary and side reactions which, at higher temperatures, are responsible for ether splitting, necessitating a further alkylation step in order to produce an oxindole ether if desired in the subsequent course of the reaction, quantitative separation of the aluminium hydroxide produced by hydrolysis presents problems.

The object of the present invention is thus to propose a process which can be used on an industrial scale or large scale for preparing 1,3-dialkyl-5-hydroxyoxindoles and the ether derivatives thereof according to formula 2, which overcomes the disadvantages known from the prior art.

According to the invention, this objective is achieved by mixing N-alkyl-p-alkoxy-(α-haloacylanilides) of formula 2

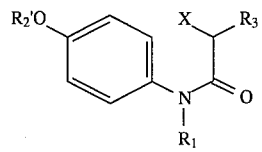

wherein $R_1$ denotes $C_{1-6}$-alkyl,
$R_2$ denotes $C_{1-6}$-alkyl,
$R_3$ denotes $C_{1-6}$-alkyl and
X denotes chlorine or bromine, with 1 to 2.5 mol (the molar data relate to one mol of the anilide of type 2 used)—preferably 1.75 to 2 mol—of an anhydrous zinc halide—preferably zinc chloride or zinc bromide—and reacting the mixture at a temperature in the range from 120° to 180° C., preferably 130° to 175° C. and more preferably in the range from 145° to 160° C. The reaction time depends on whether the reaction is carried out in substance or in a solvent. In the former case, the reaction times range from 1 to 7, preferably 2 to 5 and more preferably from 3 to 4 hours. If solvents are used, the reaction times are increased to 7 to 20, preferably 8 to 16 and more particularly 10 to 16 hours. The reaction mixture is hydrolysed after the reaction has ended and the oxindole derivative of general formula 1 ($R_2$=H) thus prepared is isolated.

In order to prepare the etherified derivatives ($R_2$=$C_{1-6}$-alkyl) all that is necessary is to use an inert solvent which has no harmful effect on the reaction of cyclisation. Thus, it is preferable to use solvents which are inert under the reaction conditions applied, of which chlorobenzene and toluene are particularly preferred.

By adding 1 mol of an organic base per mol of N-methyl-p-alkoxy-(α-halopropionyl)-anilide, preferably in admixture with zinc halide and solvent, the ether splitting can be suppressed almost entirely. Preferably, 2 to 3 mol of zinc chloride or zinc bromide are used per mol of N-methyl-p-alkoxy-(α-halopropionyl)-anilide. The reaction times are thus increased and range from 15 to 30, preferably 16 to 24 hours. It is preferable to use organic nitrogen bases, more especially trialkylamines—such as triethylamine—N,N-dialkylanilines and heterocyclic bases, such as pyridine or quinoline.

The objective described hereinbefore is achieved in particular by means of the Examples which follow. Various additional features, embodiments of the process and the like which are associated with the present invention will become apparent to those skilled in the art from the present specification and will be more readily comprehensible in conjunction with the Examples which illustrate the currently preferred embodiments of the invention by way of example. However, it is expressly pointed out that the Examples and the associated description are provided purely for the purposes of explanation and description and are not to be regarded as constituting a restriction of the invention.

EXAMPLE 1

75.6 g (0.25 mol) of N-methyl-p-methoxy-(α-bromopropionyl) anilide and 59.6 g (0.437 mol) of anhydrous zinc chloride are placed in a 250 ml three-necked flask with a mechanical stirrer and a gas outlet pipe leading to a gas washer. The temperature is increased, as the mixture is stirred, whereupon the reaction mixture becomes increasingly thinner. From a temperature of 145° C. the spontaneous development of gas begins and the sump temperature briefly rises to 160° C. As the temperature subsequently falls the reaction mixture is maintained at a temperature of 160° C. by heating for 3 hours. Then 50 ml of water are metered in within 5 minutes and the mixture is then poured into 300 ml of water. After the mixture has been stirred for 10 minutes and cooled to 20° C. the crystals formed are filtered from the suspension and dried. 41.0 g (92.55% of theory) of dark-grey 1,3-dimethyl-5-hydroxy-oxindole are obtained.

EXAMPLE 2

The method is as described in Example 1; the reaction mixture of 226.8 g (0.75 mol) of N-methyl-p-methoxy-(α-bromopropionyl) anilide and 178.9 (1.31 mol) of zinc chloride is heated to 65° C. with stirring until it flows easily. Then some of it (about 20%) is metered into a 750 ml reaction vessel arranged underneath, preheated to 160° C. (equipped with stirrer and gas outlet). After the reaction has started (from 145° C.) and the spontaneous development of gas has died down the majority of the reaction mixture is metered out of the upper vessel within 70 minutes. In all, the reaction mixture is heated to 160° C. for three hours. Processing is as described in Example 1. Yield: 124.8 g (93.9% of theory) of crude 1,3-dimethyl-5-hydroxy-oxindole.

Recrystallisation of 100 g of crude material is carried out using 1480 ml of methanol. It is dissolved hot, with the addition of 5.4 g of activated charcoal, and filtered. After the filtrate has been evaporated down to 150 ml it is cooled to a temperature of −25° C. over a period of about 12 hours. The crystals precipitated are suction filtered and dried. In this way the 1,3-dimethyl-5-hydroxyoxindole is obtained in a yield of 69.5 g (69.5% of the material put in) in the form of crystals with a melting point of 207°–209° C.

EXAMPLE 3

The procedure is again as described in Example 1: the full amount of zinc chloride (28.6 g; 0.21 mol is heated with part (about 20%) of the N-methyl-p-methoxy-(α-bromopropionyl)anilide (6.5 g; 0.024 mol) to a temperature of 145°–160° C. After the development of gas has died down the majority of the anilide (26.1 g; 0.096 mol) is metered into the reaction mixture within 60 minutes and heated to a temperature of 160° C. for a total of three hours. Processing is carried out as described in Example 1. In this way the 1,3-dimethyl-5-hydroxyoxindole is isolated in a crude yield of 18.22 g (85.7% of theory).

EXAMPLE 4

Analogously to Example 1: 14.95 g (0.05 mol) of N-methyl-p-ethoxy-(α-bromopropionyl) anilide are heated to a temperature of 160°–165° C. for 90 minutes and then worked up according to Example 1. Yield: 8.2 g (92.5% of theory) of crude 1,3-dimethyl-5-hydroxy-oxindole.

EXAMPLE 5

The procedure is as in Example 1: 38.2 g (0.15 mol) of N-methyl-p-ethoxy-(α-chloropropionyl)-anilide and 35.77 g (0.2625 mol) of zinc chloride are heated with stirring. The reaction begins at 135° C. The reaction temperature is maintained at 145°–150° C. for a period of 110 minutes. After working up analogously to Example 1, 24.2 g (91.0% of theory) of crude 1,3-dimethyl-5-hydroxy-oxindole are isolated.

EXAMPLE 6

14.96 g (0.05 mol) of N-methyl-p-ethoxy-(α-bromopropionyl)-α-anilide and 13.63 g (0.1 mol) of anhydrous zinc chloride in 100 ml of chlorobenzene are refluxed for 10 hours with stirring. After cooling to 50° C. the reaction mixture is twice stirred with 20 ml of water. Then the organic phase is twice stirred with 40 ml of dilute potassium hydroxide solution (2.5% strength) and with 30 ml of water. The organic phase is isolated and evaporated down to a residue. Crystallisation of the residue (7.1 g) is effected from a mixture of 30 ml of cyclohexane and 2 ml of acetone. 5.58 g (54.3% of theory) of 1,3-dimethyl-5-ethoxy-oxindole are obtained. The combined alkaline aqueous phases are mixed with sulphuric acid. A crystal precipitate settles out of the acid solution (pH 1). After drying, 1.76 g (19.9% of theory) of 1,3-dimethyl-5-hydroxy-oxindole are obtained.

EXAMPLE 7

The method is as in Example 6: 12.73 g (0.05 mol) of N-methyl-p-ethoxy-(α-chloropropionyl) anilide and 13.63 g (0.1 mol) of zinc chloride in 20 ml of chlorobenzene are refluxed for 8 hours with stirring. After processing, as described in Example 6, 3.16 g (33.9% of theory) of 1,3-dimethyl-5-ethoxyoxindole and 2.78 g (31.4% of theory) of 1,3-dimethyl-5-hydroxy-oxindole are obtained.

EXAMPLE 8

The method is as described in Example 6: 7.45 g (0.025 mol) of N-methyl-p-ethoxy-(α-bromopropionyl)anilide, 10.2 g (0.075 mol) of anhydrous zinc chloride and 2.53 g (0.025 mol) of triethylamine in 50 ml of chlorobenzene are refluxed for 24 hours with stirring. After cooling the mixture is worked up as described in Example 6. In order to separate off all the triethylamine, the first quantity of water is additionally acidified with hydrochloric acid. 4.05 g (79% of theory) of crude 1,3-dimethyl-5-ethoxy-oxindole are obtained.

EXAMPLE 9

The method is as in Example 8: 7.45 g (0.025 mol) of N-methyl-p-ethoxy-(α-bromopropionyl)-anilide, 16.9 g (0.075 mol) of anhydrous zinc bromide and 2.59 g (0.025 mol) of triethylamine in 40 ml of chlorobenzene are refluxed for 24 hours with stirring. After working up as in Example 8, 4.79 g (93.4% of theory) of crude 1,3-dimethyl-5-ethoxy-oxindole are obtained.

What is claimed is:

1. A process for preparing a 1,3-dialkyl-5-hydroxyoxindole of formula 1:

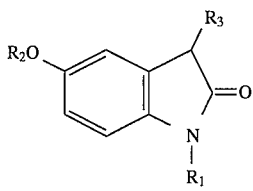

wherein $R_1$ denotes $C_1$–$C_6$-alkyl, $R_2$ denotes hydrogen, and $R_3$ denotes $C_1$–$C_6$-alkyl, comprising heating an N-alkyl-p-alkoxy-(α-haloacyl)anilide of formula 2:

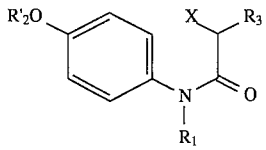

wherein $R_1$ denotes $C_1$–$C_6$-alkyl, $R'_2$ denotes $C_1$–$C_6$-alkyl, $R_3$ denotes $C_1$–$C_6$-alkyl, and X denotes chlorine or bromine, in the presence of an anhydrous zinc halide to a temperature in the range from about 120° C. to about 160° C., and isolating the 1,3-dialkyl-5-hydroxyoxindole prepared.

2. The process of claims 1 in which the anhydrous zinc halide is zinc chloride or zinc bromide.

3. The process of claim 1 in which an inert polar solvent is present.

4. The process of claim 3 in which an organic nitrogen base is present.

5. The process of claim 1 in which 1 to 2.5 mol of anhydrous zinc halide per mol of N-alkyl-p-alkoxy-(α-haloacyl) anilide is present.

6. The process of claim 1 in which the temperature is in the range of 145° C. to 160° C.

7. A process for preparing a 1,3-dialkyl-5-alkoxyoxindole of formula 1:

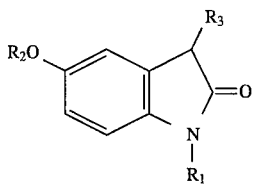

wherein $R_1$ denotes $C_1$–$C_6$-alkyl, $R_2$ denotes $C_1$–$C_6$-alkyl, and $R_3$ denotes $C_1$–$C_6$-alkyl, comprising heating an N-alkyl-p-alkoxy-(α-haloacyl) anilide of formula 2:

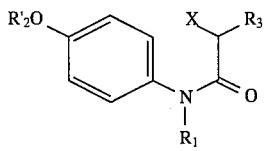

wherein $R_1$ denotes $C_1$–$C_6$-alkyl, $R'_2$ denotes $C_1$–$C_6$-alkyl, $R_3$ denotes $C_1$–$C_6$-alkyl, and X denotes chlorine or bromine, in an inert polar solvent in the presence of an anhydrous zinc halide to a temperature in the range from about 120° C. to about 180° C., and isolating the 1,3-dialkyl-5-alkoxyoxindole prepared.

8. The process of claim 7 in which the anhydrous zinc halide is zinc chloride or zinc bromide.

9. The process of claim 7 in which the inert solvent is chlorobenzene or toluene.

10. A process for preparing a 1,3-dialkyl-5-alkoxyoxindole of formula 1:

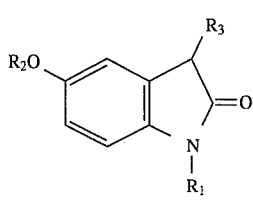

wherein $R_1$ denotes $C_1$–$C_6$-alkyl, $R_2$ denotes $C_1$–$C_6$-alkyl, and $R_3$ denotes $C_1$–$C_6$-alkyl, comprising heating an N-alkyl-p-alkoxy-(α-haloacyl)anilide of formula 2:

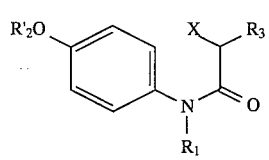

wherein $R_1$ denotes $C_1$–$C_6$-alkyl, $R'_2$ denotes $C_1$–$C_6$-alkyl, $R_3$ denotes $C_1$–$C_6$-alkyl, and X denotes chlorine or bromine, to a temperature in the range from about 120 ° C. to about 180 ° C. in an inert solvent in the presence of an anhydrous zinc halide and an organic base and isolating the 1,3-dialkyl-5-alkoxyoxindole prepared.

11. The process of claim 10 in which the organic base is a nitrogen compound selected from the group consisting of a trialkylamine, an N,N-dialkylaniline, pyridine or quinoline.

12. The process of claim 10 in which the trialkylamine is triethylamine.

13. The process of claim 10 in which the temperature is in the range of from about 130° C. to about 175° C. and 2.0 to 3.0 mol of anhydrous zinc halide per mol of N-alkyl-p-alkoxy-(α-haloacyl)anilide is present.

14. The process of claim 13 in which the anhydrous zinc halide is zinc chloride or zinc bromide.

15. The process of claim 11 in which the temperature is in the range of 145° C. to 160° C.

* * * * *